(12) United States Patent
Kusumi et al.

(10) Patent No.: US 8,192,417 B2
(45) Date of Patent: Jun. 5, 2012

(54) DISPOSABLE PANTS

(75) Inventors: Takao Kusumi, Osaka (JP); Masaru Fujioka, Tokushima (JP)

(73) Assignee: Livedo Corporation, Ehime (JP)

( * ) Notice: Subject to any disclaimer, the term of this patent is extended or adjusted under 35 U.S.C. 154(b) by 450 days.

(21) Appl. No.: 11/667,695

(22) PCT Filed: Nov. 24, 2005

(86) PCT No.: PCT/JP2005/021584
§ 371 (c)(1),
(2), (4) Date: May 14, 2007

(87) PCT Pub. No.: WO2006/057301
PCT Pub. Date: Jun. 1, 2006

(65) Prior Publication Data
US 2008/0015534 A1    Jan. 17, 2008

(30) Foreign Application Priority Data

Nov. 24, 2004   (JP) ................................ 2004-338643

(51) Int. Cl.
*A61F 13/15* (2006.01)
(52) U.S. Cl. ................... 604/387; 604/389; 604/385.03; 604/385.01
(58) Field of Classification Search .................. 604/383, 604/385.01, 385.03, 396
See application file for complete search history.

(56) References Cited

U.S. PATENT DOCUMENTS

| 6,508,799 | B1 | 1/2003 | Freiburger et al. |
| 7,077,834 | B2 * | 7/2006 | Bishop et al. ............ 604/385.11 |
| 2002/0165514 | A1 * | 11/2002 | Datta et al. ............... 604/385.11 |
| 2003/0088223 | A1 * | 5/2003 | Vogt et al. ................ 604/385.01 |
| 2003/0220626 | A1 | 11/2003 | Karami |
| 2004/0039364 | A1 | 2/2004 | Karami |

FOREIGN PATENT DOCUMENTS

| EP | 1 559 387 | 8/2005 |
| EP | 1 698 313 | 9/2006 |
| JP | 1-141711 | 9/1989 |
| JP | 5-317356 | 3/1993 |
| JP | 8-229072 | 9/1996 |
| JP | 2003-528650 | 9/2003 |
| WO | 02/083050 | 10/2002 |
| WO | 03/024375 | 3/2003 |

OTHER PUBLICATIONS

Extended European Search Report issued Aug. 9, 2011, in European Application No. 05 80 9452.

* cited by examiner

*Primary Examiner* — Michele M Kidwell
(74) *Attorney, Agent, or Firm* — Wenderoth, Lind & Ponack, L.L.P.

(57) ABSTRACT

A pair of disposable pants includes a front abdominal section and a rear section joined almost annularly, and a crotch section provided to be joined between the front abdominal section and rear section. Breaking line parts are provided on the front abdominal section for breaking it into a central front abdominal part and left and right front abdominal parts. Adhesive pieces are provided on the left and right front abdominal parts for connecting the central front abdominal part and the left and right front abdominal parts. The adhesive pieces are provided on the interior side of the front abdominal section, and the breaking line parts are exposed to the outside.

19 Claims, 11 Drawing Sheets

DISPOSABLE PANTS

BACKGROUND OF INVENTION

1. Field of Invention

The present invention relates to disposable pants which can be used as pants, a diaper and the like.

2. Description of the Related Art Japanese Patent Application Laid-Open No. 5-317356 discloses conventional disposable pants of this type. In the pants described in Japanese Patent Application Laid-Open No. 5-317356, breaking lines are provided on both left and right sides of a front section to allow the front section to be separated at the breaking lines, and adhesive pieces are provided at bonding parts on the left and right sides of the front section and a rear section. When the front section is separated at the breaking lines, the front section and rear section are fastened by the left and right adhesive pieces.

SUMMARY OF THE INVENTION

However, in the pants disclosed in the above publication, the breaking lines are located in positions hidden by the adhesive pieces. This arrangement makes recognition of the breaking lines difficult, and the adhesive pieces obstruct the breaking operation.

The present invention has an object to provide disposable pants allowing easy recognition of the breaking line parts and an easy breaking operation.

Disposable pants according to a first embodiment of the present invention comprise a front abdominal section and a rear section joined almost annularly, a crotch section between the front abdominal section and rear section, and an absorber provided on the crotch section, wherein breaking line parts are provided on the front abdominal section for breaking it into a central front abdominal part almost in the center, and left and right front abdominal parts. Adhesive pieces are provided on the central front abdominal part, or the left and right front abdominal parts for connecting the central front abdominal part and the left and right front abdominal parts. The adhesive pieces are formed such that the breaking line parts are exposed to the outside.

According to the first embodiment of the disposable pants of the present invention, the adhesive pieces are formed such that the aforementioned breaking line parts are exposed to the outside, which allows the breaking line parts to be easily recognized from the outside. Further, the adhesive pieces are unlikely to obstruct breaking at the breaking line parts, which allows the breaking operation to be carried out easily.

In this case, for example, the adhesive pieces may be provided on the interior side of the aforementioned central front abdominal part or on the interior side of the left and right front abdominal parts.

When the adhesive pieces are provided in this manner on the interior side of the aforementioned central front abdominal part or the interior side of the left and right front abdominal parts, the breaking line parts can be easily recognized from the outside. Further, the adhesive pieces are unlikely to obstruct breaking at the breaking line parts, which allows the breaking operation to be carried out easily.

Further, in this case, on one side surface of the adhesive pieces, adhesive parts detachably attachable to portions on the side of the central front abdominal part or to portions on the side of the left and right front abdominal parts may be provided. The adhesive parts may be provided in areas laterally inward from the outer edges of the adhesive pieces.

Accordingly, contact between the outer edges of the adhesive parts and the wearer's skin, etc. can effectively be prevented.

Further, for instance, the adhesive pieces may be provided on the exterior side of the central front abdominal part or on the exterior side of the left and right front abdominal parts, and may be folded such that the breaking line parts are exposed to the outside.

Accordingly, the breaking line parts can be easily recognized from the outside. Further, the adhesive pieces are unlikely to obstruct breaking at the breaking line parts, which allows the breaking operation to be carried out easily. In addition, there is an advantage in that the adhesive pieces can be easily recognized from the outside.

In this case, the adhesive pieces may be folded such that tips of the adhesive pieces are folded toward the inside.

Accordingly, the tips of the adhesive pieces are unlikely to be loose.

Further, the adhesive pieces may be provided on the interior side of the left and right front abdominal parts, the adhesive parts may be provided on the interior side of projections which are tips of the adhesive pieces, and the projections may be folded back.

The disposable pants can be used similar to a developed-type diaper or pants-type diaper, and is further unlikely to cause unintentional release of a portion arranged on the abdominal side, and furthermore, has a high degree of flexibility in size adjustment.

Further, the left and right front abdominal parts and the rear section may have stretchability in their left and right directions.

Accordingly, the left and right front abdominal parts and the rear section can closely fit the waist.

Further, a loop-side member may be provided on the central front abdominal part, and the adhesive parts may be hook-side members detachably engageable with the loop-side member.

Further, a second adhesive part may be provided on both sides of the crotch section on the edges of the front abdominal section, and the second adhesive part may be detachably secured to an adhesive part on the interior side of the adhesive pieces.

Accordingly, the front abdominal section can effectively be prevented from becoming crinkled or displaced.

These and other objects, features, aspects and advantages of the present invention will become more apparent from the following detailed description and accompanying drawings.

DETAILED DESCRIPTION OF THE INVENTION

Figure 1:
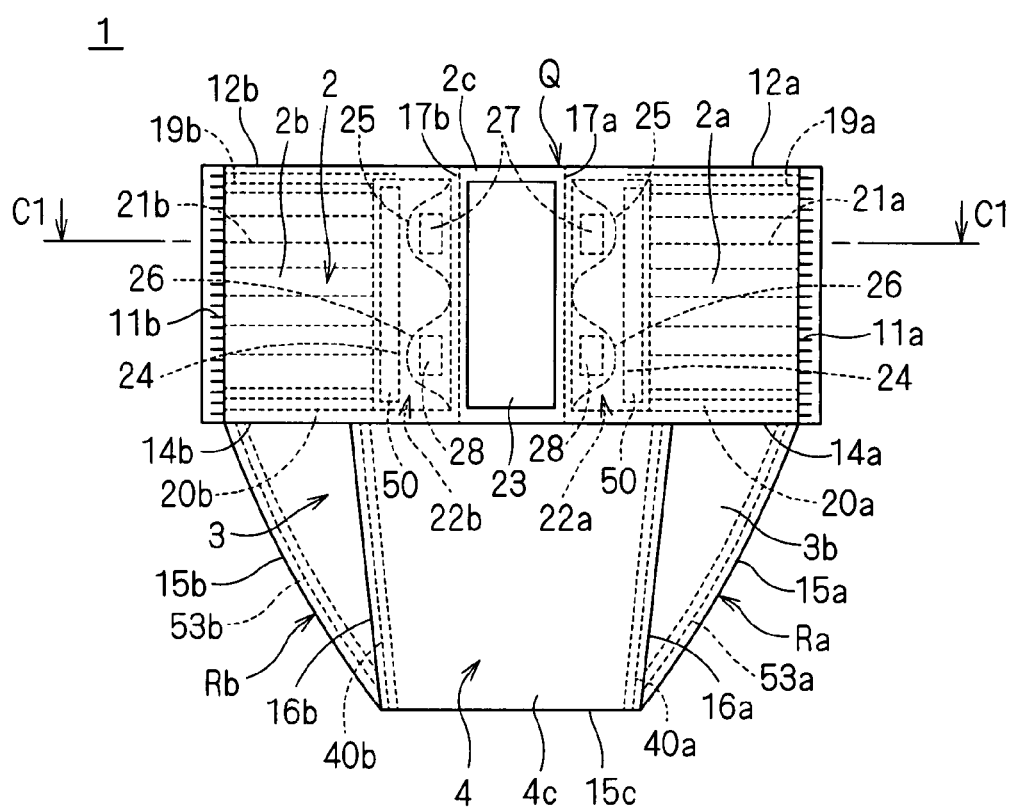
FIG. 1 is a front view showing disposable pants according to a first embodiment of the present invention.

Hereinafter, disposable pants according to the present invention will be described.

The disposable pants comprise breakable breaking line parts and adhesive pieces for connecting broken portions. The adhesive pieces are formed in a manner such that the aforementioned breaking line parts are exposed to the outside before breaking.

Hereinafter, more specific description will be given of each embodiment with reference to the drawings.

First Embodiment

<General Description>

With reference to FIGS. 1 to 8, disposable pants 1 according to a first embodiment of the present invention will be described. In the first embodiment, adhesive pieces 22a and 22b are provided on the inner side of breaking line parts 17a and 17b. The disposable pants 1 are configured to comprise a front abdominal section 2 and a rear section 3 joined almost annularly, and a crotch section 4 provided to be joined between the front abdominal section 2 and rear section 3, and are usable as both pants and a diaper. In the description of the disposable pants 1, the left and right shall indicate the left hand side and right hand side as viewed from a wearer.

The front abdominal section 2 and rear section 3 refer to portions of the disposable pants 1 that mainly face the front abdominal area and area on the back of a wearer, respectively. Left and right edges of the front abdominal section 2 and left and right edges of the rear section 3 are bonded to each other, and the front abdominal section 2 and rear section 3 are thereby joined almost annularly. Accordingly, a left side bonding part 11a and a right side bonding part 11b for bonding the left and right edges of the front abdominal section 2 and left and right edges of the rear section 3 are formed on left and right edges of the disposable pants 1. Bonding at these side bonding parts 11a and 11b is created either by bonding with an adhesive such as a hot melt adhesive, or ultrasonic welding (or heating welding), or by both of them in combination.

The crotch section 4 indicates a portion of the disposable pants 1 that mainly faces the crotch of a wearer, having a front crotch part 4a and a rear crotch part 4b joined to the front abdominal section 2 and rear section 3, respectively. In this embodiment, the front crotch part 4a and rear crotch part 4b of the crotch section 4 are bonded to the front abdominal section 2 and rear section 3 by an adhesive such as a hot melt adhesive. As a variation, the crotch section 4 may be formed integrally by a member connected to one or both of the front abdominal section 2 and rear section 3.

A waist opening Q is formed when upper edges 12a, 12b and 13 of the front abdominal section 2 and rear section 3 are joined almost annularly as described. A left leg opening Ra is formed by a lower edge 14a of a left front abdominal part 2a of the front abdominal section 2, a sloped edge 15a on the left lower side of the rear section 3 and a left edge 16a of the crotch section 4. A right leg hole Rb is formed by a lower edge 14b of a right front abdominal part 2b of the front abdominal section 2, a sloped edge 15b on the right lower side of the rear section 3, and a right edge 16b of the crotch section 4.

<Front Abdominal Section>

The front abdominal section 2 has an almost laterally-long rectangular shape in plan view (cf. FIG. 1), and includes the left front abdominal part 2a, right front abdominal part 2b and a central front abdominal part 2c positioned between them. The central front abdominal part 2c corresponds to a central area of the present invention. A left breaking line part 17a extending vertically through the front abdominal section 2 is formed between the left front abdominal part 2a and central front abdominal part 2c, and a right breaking line part 17b extending vertically through the front abdominal section 2 is formed between the right front abdominal part 2b and central front abdominal part 2c. A bonding part 18 to the front crotch part 4a of the crotch section 4 is formed in the central front abdominal part 2c (cf. FIG. 5). Bonding at the bonding part 18 is created with an adhesive such as a hot melt adhesive.

The left and right breaking line parts 17a and 17b are formed laterally inward from the side edges of the front crotch part 4a. Here, the adhesive pieces 22a and 22b are attached in a folded manner laterally inward from the side edges of the front crotch part 4a, and the left and right breaking line parts 17a and 17b are formed so as to extend along the inner side edges of these adhesive pieces 22a and 22b. The breaking line parts 17a and 17b are weakened as compared to areas therearound, and are formed, for example, by subjecting the front abdominal section 2 to linear heating (e.g., heat sealing), or intermittent cutting to provide perforations, or linear ultrasonic treatment (e.g., ultrasonic sealing). By breaking these breaking line parts 17a and 17b, the front abdominal section 2 can be separated at the breaking line parts 17a and 17b (cf. FIGS. 2 to 4). The front abdominal section 2 is thereby broken into the central front abdominal part 2c almost in the center and left and right front abdominal parts 2a, 2b on the left and right thereof at the position to which the crotch section 4 is joined. The breaking line parts 17a and 17b may be formed linearly or may be formed as curved lines according to necessity. Alternatively, a plurality of linearly weakened parts may be formed in parallel to constitute each of the breaking line parts 17a and 17b.

Waist elastic members 19a and 19b are attached in a laterally stretched state to the upper edges 12a and 12b of the left front abdominal part 2a and right front abdominal part 2b. Leg elastic members 20a and 20b are attached in a laterally stretched state to the lower edges 14a, 14b of the left front abdominal part 2a and right front abdominal part 2b. Body elastic members 21a and 21b are attached in a laterally stretched state to areas between the upper edges 12a and 12b and lower edges 14a and 14b of the left front abdominal part 2a and right front abdominal part 2b. Contraction and stretch of these elastic members 19a, 19b, 20a, 20b, 21a and 21b allows the front abdominal section 2 (particularly, left front abdominal part 2a and right front abdominal part 2b) to fit snugly about the wearer's abdominal area.

Figure 5:
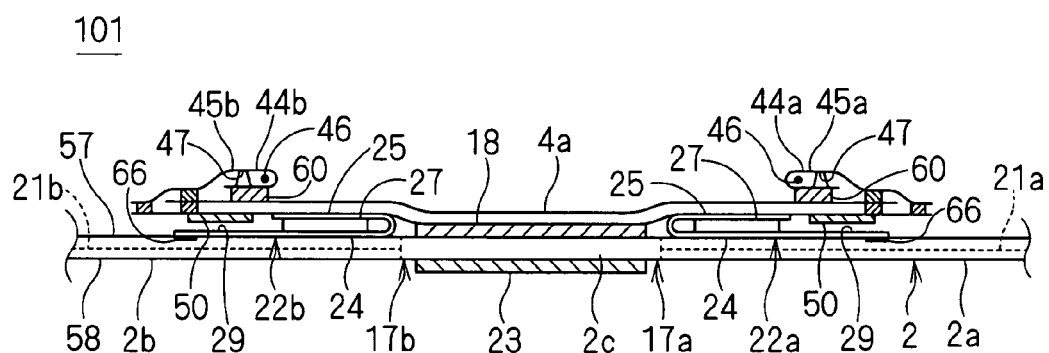
FIG. 5 is an enlarged view showing breaking line parts.

Such front abdominal section 2 is formed by sandwiching the elastic members 19a, 19b, 20a, 20b, 21a and 21b between an interior-layer sheet 57 which faces the wearer's abdominal area, and an exterior-layer sheet 58 on the exterior side (cf. FIGS. 1 and 5).

Almost sheet-like left adhesive piece 22*a* and right adhesive piece 22*b* are bonded to the edges of the left front abdominal part 2*a* and right front abdominal part 2*b*, respectively, on the interior side thereof (i.e., facing the wearer's abdominal area), and on the side of the central front abdominal part 2*c*, by an adhesive such as a hot melt adhesive (cf. FIGS. 1 to 6).

This Adhesive pieces 22*a* and 22*b* are on the interior sides of the left front abdominal part 2*a* and the right front abdominal part 2*b* when the diaper is in the form of pants before breaking at the breaking line parts 17*a* and 17*b*. Besides, portions of the adhesive pieces 22*a* and 22*b* that extend beyond the breaking line parts 17*a* and 17*b* (here, projections 25 and 26 which will be described later) are folded to be folded back toward their base sides (cf. FIGS. 1 and 5).

Figure 7:
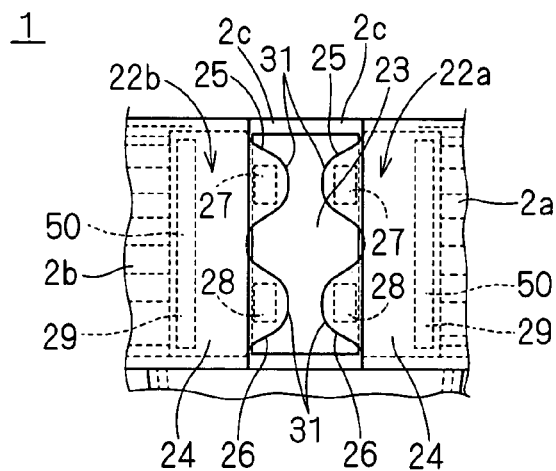
FIG. 7 is a sectional view taken along line C2-C2 of the disposable pants shown in FIG. 3.
Figure 8:
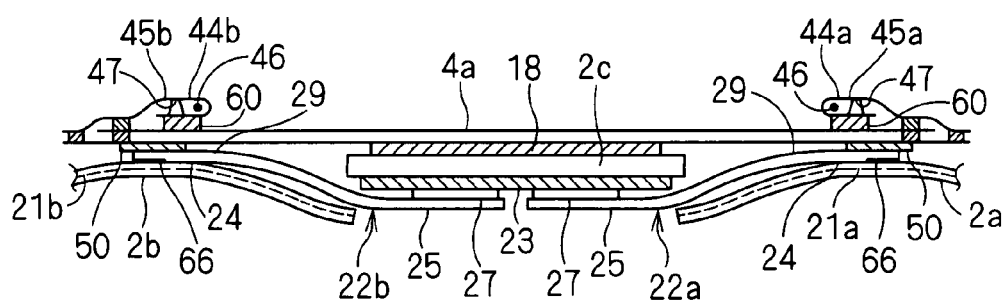
FIG. 8 is a diagram showing the state in which left and right adhesive pieces are secured to a central front abdominal part.
Figure 9:
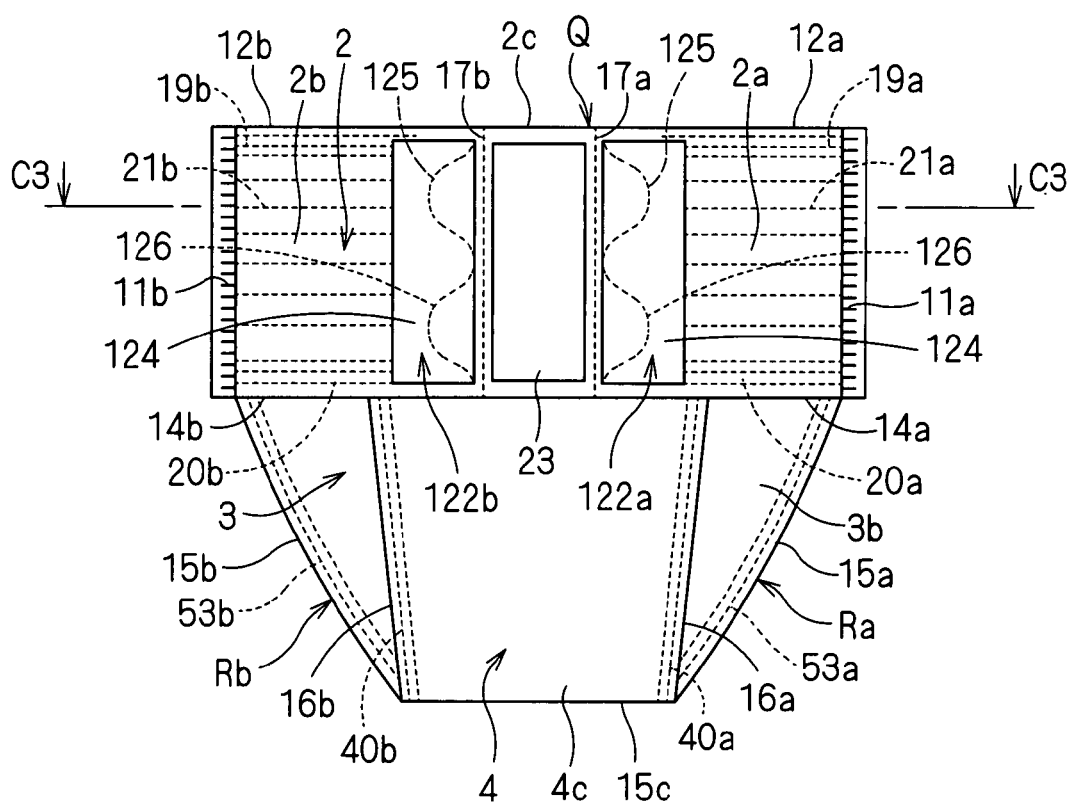
FIG. 9 is a front view of disposable pants according to a second embodiment of the present invention.
Figure 10:
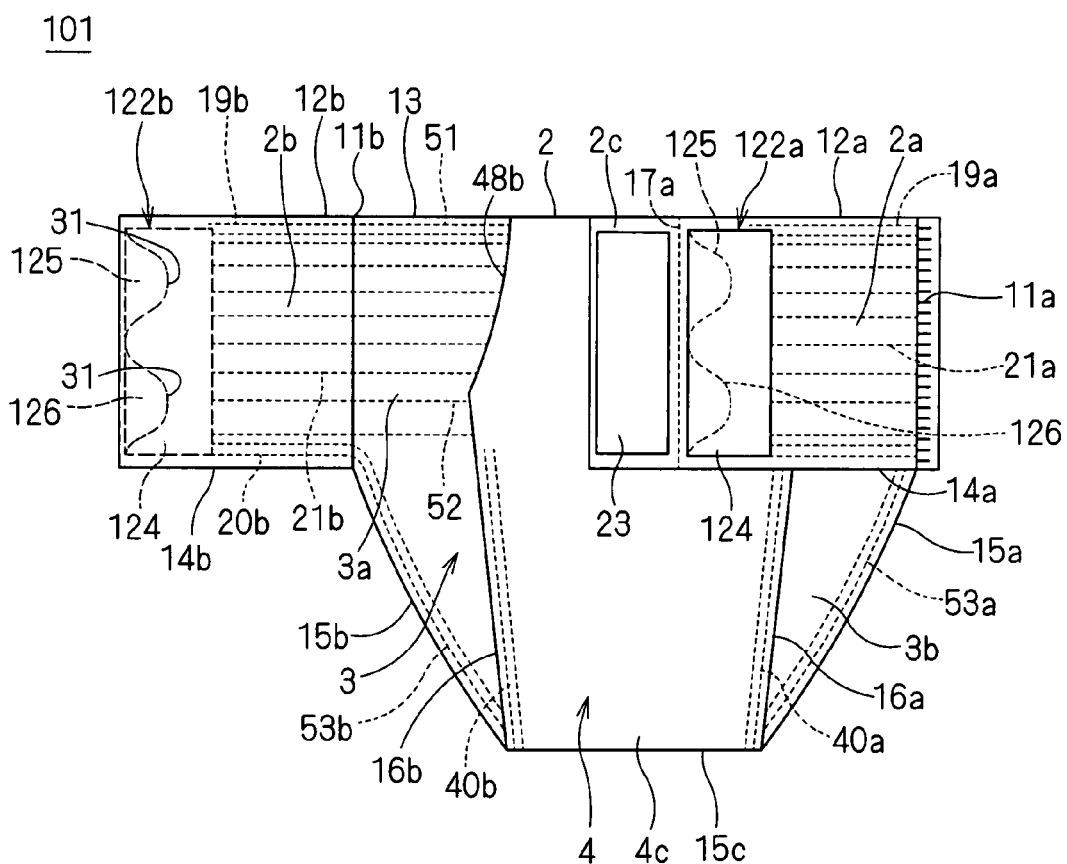
FIG. 10 is a diagram showing the state in which a right breaking line part of the disposable pants shown in FIG. 9 is broken to develop a right front abdominal part.
Figure 11:
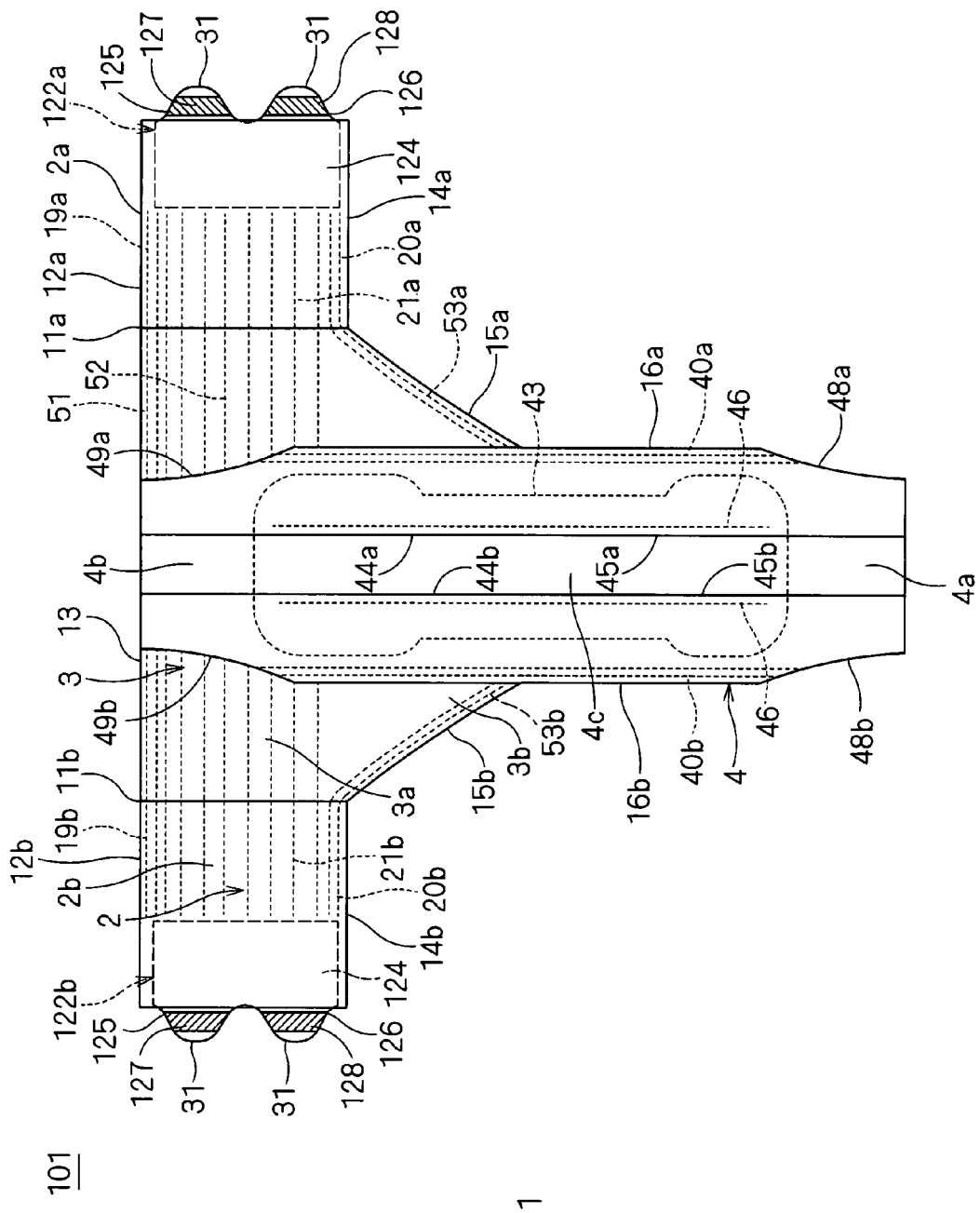
FIG. 11 is a diagram showing the state in which a crotch section of the disposable pants shown in FIG. 9 is developed.
Figure 12:
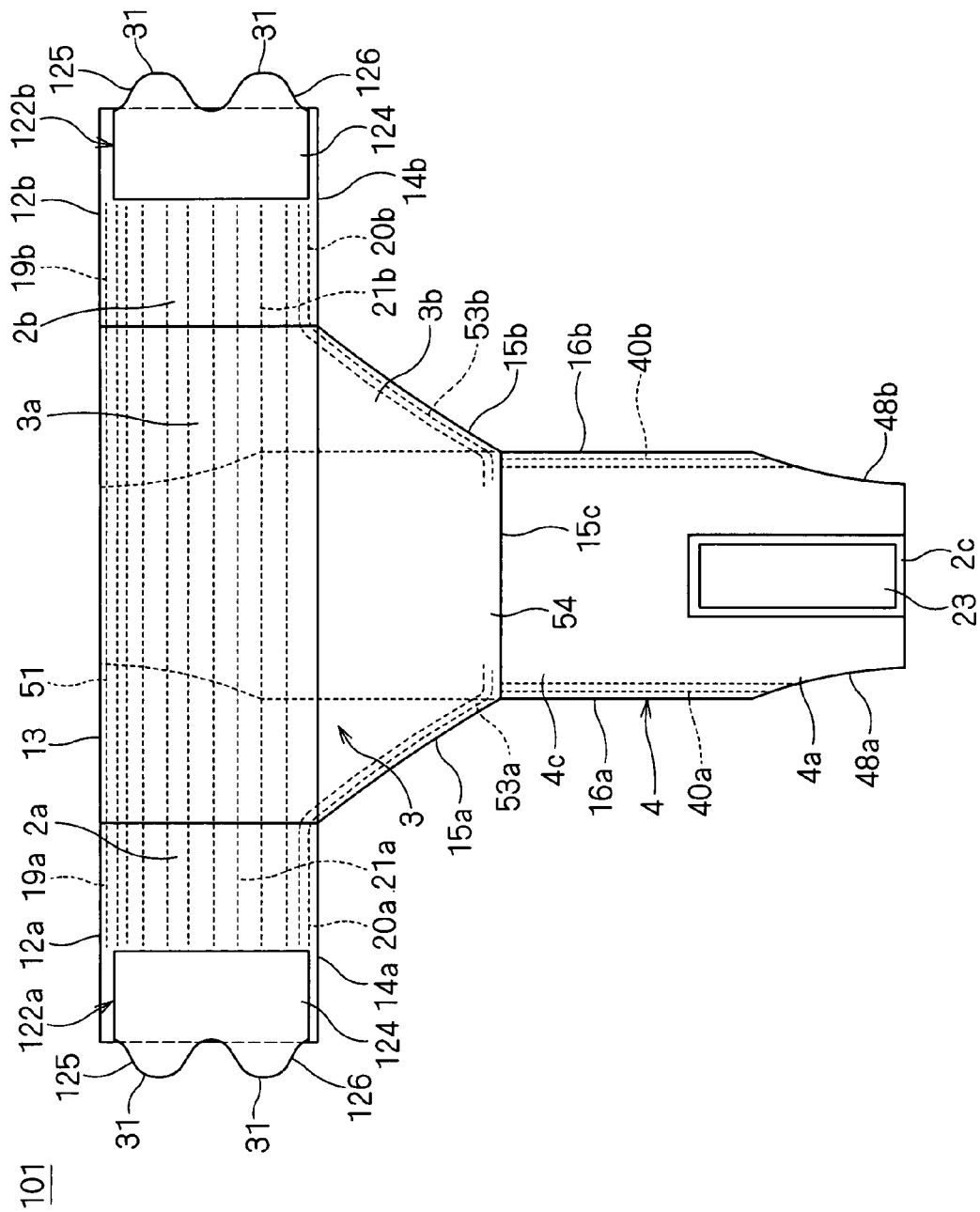
FIG. 12 is a diagram of the disposable pants shown in FIG. 11 as viewed from the opposite side to FIG. 11.

When breaking the breaking line parts 17*a* and 17*b* to use the diaper in the form of a diaper, the adhesive pieces 22*a* and 22*b* extend out from the edges of the left front abdominal part 2*a* and right front abdominal part 2*b* to be detachably attached to the exterior surface of an adhesive part 23 which will be described next (cf. FIGS. 7 and 8).

On the exterior side of the central front abdominal part 2*c*, a planar adhesive part 23, as a first adhesive part to which the adhesive pieces 22*a* and 22*b* are to be attached, is provided. This adhesive part 23 has its width set at or smaller than the distance between the left and right breaking line parts 17*a* and 17*b* (i.e., lateral dimension of central front abdominal part 2*c*) and its height set almost equal to the vertical dimension of the adhesive pieces 22*a* and 22*b*.

The adhesive pieces 22*a* and 22*b* each include an almost vertically long strip body 24 and two projections 25 and 26, one on top of the other extending from the free edge side of the body 24. The laterally outside edges of the body 24 are bonded to the interior side of the left front abdominal part 2*a* and right front abdominal part 2*b*, close to the edges thereof and on the side of the breaking line parts 17*a* and 17*b*, by an adhesive 66, e.g., hot melt adhesive (cf. FIG. 5).

Adhesive parts 27 and 28 are provided on the interior side (side facing the adhesive part 23 when the pants are in the form of diaper) on each of the respective projections 25 and 26 of the adhesive pieces 22*a* and 22*b*. Here, the respective projections 25 and 26 as leading edges of the adhesive pieces 22*a* and 22*b* are folded back, and the adhesive parts 27 and 28 are directed to the exterior side of the front abdominal section 2. Besides, the adhesive parts 27 and 28 are provided in areas laterally inward from the outer edges of the adhesive pieces 22*a* and 22*b*. Here, the adhesive parts 27 and 28 are formed in an almost square shape which is smaller than the respective projections 25 and 26, and the adhesive parts 27 and 28 are attached to one side surface of the respective projections 25 and 26 so as not to overlap their outer edges. The aforementioned adhesive pieces 22*a* and 22*b* are detachably secured to the adhesive part 23 with the adhesive parts 27 and 28 interposed therebetween.

Portion on the interior side of the body 24 of adhesive pieces 22*a* and 22*b*, are also formed as an adhesive part 29. An adhesive part 50 which will be described later, is configured to be detachably secured to the adhesive part 29 on the interior side of the body 24 of the adhesive pieces 22*a* and 22*b* in the state where the adhesive parts 27 and 28 on the projections 25 and 26 of the adhesive pieces 22*a* and 22*b* are secured to the aforementioned adhesive part 23 (cf. FIGS. 7 and 8).

Further, on the other side surface (exterior surface) of the adhesive pieces 22*a* and 22*b* opposite to the surface on which the aforementioned adhesive parts 27 and 28 are provided is also formed as an adhesive part. This adhesive part is configured to allow the aforementioned adhesive parts 27 and 28 to be detachably attached thereto.

Then, in the state where a first adhesive piece 22*a* (or 22*b*) is secured to the adhesive part 23 with the adhesive parts 27 and 28 interposed therebetween, the second adhesive piece 22*b* (or 22*a*) can be secured so as to overlap the first adhesive piece 22*a* (or 22*b*).

The adhesive parts may be provided on part of, or on the entire area of the exterior side of the adhesive pieces 22*a* and 22*b*, but an arrangement so as to include the tips of the projections 25 and 26 brings a bigger advantage in easily fixing the adhesive pieces 22*a* and 22*b* securely while overlapping them with each other.

Specific examples of the adhesive parts 23, 29, etc. may include a loop-side member having a nonwoven fabric, a woven fabric, a knitted material or the like with a fine loop structure being densely formed on its surface. Specific examples of the adhesive parts 27, 28 and 50 may include a hook-side member with a fine hook structure in freely detachable engagement with the loop-side member being densely formed on its surface.

More specifically, as the adhesive parts 23, 29, etc., a plastic film composite material having on its surface a nonwoven fabric, a woven fabric or the like which is suitably used as a loop-side member for a hook-and-loop fastener is used for example. As the adhesive parts 23, 29, etc., a loop-side member may be attached as a separate member to the central front abdominal part 2*c* or the adhesive pieces 22*a* and 22*b*; alternatively, the exterior surface of the central front abdominal part 2*c*, or exterior or interior surface of the adhesive pieces 22*a* and 22*b* may be formed to function as a loop-side member. For that purpose, for instance, as a material for the adhesive pieces 22*a*, 22*b* or the central front abdominal part 2*c*, one having a loop structure may be selected, or alternatively, required portions on the surfaces of the adhesive pieces 22*a*, 22*b* or on the central front abdominal part 2*c* may be surface-treated to be fuzzed, or may further be treated, for example, by weaving wool into the adhesive pieces 22*a*, 22*b* or the central front abdominal part 2*c* to provide a loop structure.

As the adhesive parts 27, 28, 50, a plastic film having pins densely formed on its surface is a suitable hook-side member.

Another specific example of the adhesive parts 23, 29, etc. may include a plastic film or the like, which is surface-treated by using PEELOIL, for example, so as to have repetitive removability from an adhesive. Still another specific example may include a reusable adhesive.

In the above-described specific examples of the aforementioned adhesive parts 23, 29, etc. and those of the adhesive parts 27, 28, 50, their structures may be interchanged with each other.

Further, the tips of the respective projections 25 and 26 of the adhesive pieces 22*a* and 22*b* are formed as tabs 31 (cf. FIG. 4) for easy lifting of the adhesive pieces 22*a* and 22*b*. These tabs 31 are not provided with adhesive parts 27 and 28.

In this abdominal section 2, when breaking at the respective breaking line parts 17*a* and 17*b*, the right front abdominal part 2*b* is developed to the right integrally with the right adhesive piece 22*b*. Further, the left front abdominal part 2*a* is developed to the left integrally with the left adhesive piece 22*a*. At this time, the central front abdominal part 2*c* is kept bonded to the crotch section 4 and remains on the exterior side of the front crotch part 4*a*.

Accordingly, since the front abdominal section 2 and crotch section 4 are secured by the bonding part 18 in the state before breaking the breaking line parts 17a and 17b (at the time of product shipping), the disposable pants 1 function as pants, and are easily raised/lowered similar to typical disposable pants having no opening/closing means such as the adhesive pieces 22a and 22b, etc. (cf. FIG. 1). Besides, in this state, the front abdominal section 2 and crotch section 4 will not be separated even if the engagement between the adhesive pieces 22a, 22b and adhesive part 23 is released.

Further, in the case where the disposable pants 1 are worn as pants and when an absorber 43 to be described later absorbs and contains bodily wastes, the breaking line parts 17a and 17b are broken, so that the pants 1 can easily be removed from the wearer. In this case, the pants 1 can be removed without taking off the wearer's garments.

Further, after breaking the breaking line parts 17a, 17b to develop the front abdominal section 2 to see how the inside of the pants 1 gets soiled, the adhesive pieces 22a and 22b may be developed and extended to be engaged with the adhesive part 23, so that the pants 1 can be returned to its original state as pants. Besides, when the pants 1 and an optional pad such as a urine pad are used in combination, the adhesive pieces 22a and 22b can be attached/detached to facilitate replacing such optional pad, and the like.

Figure 2:
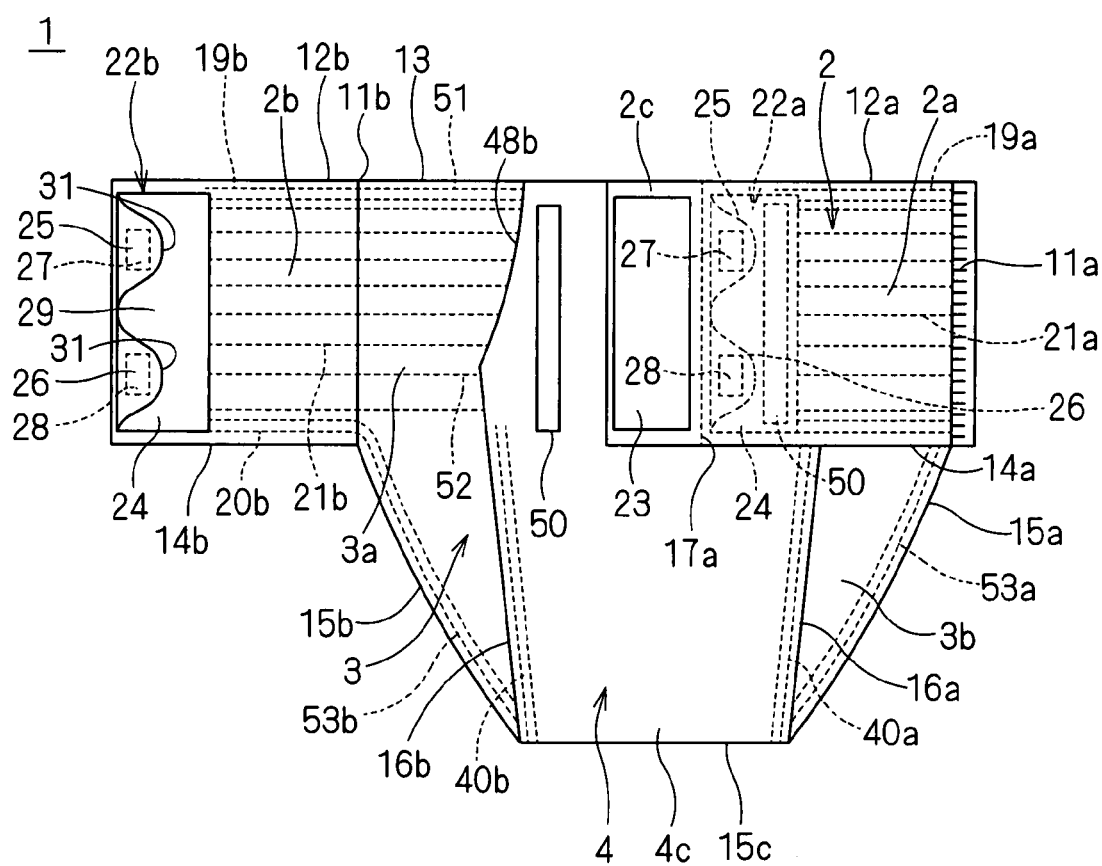
FIG. 2 is a diagram showing the state in which a right breaking line part of the disposable pants shown in FIG. 1 is broken to develop a right front abdominal part.
Figure 3:
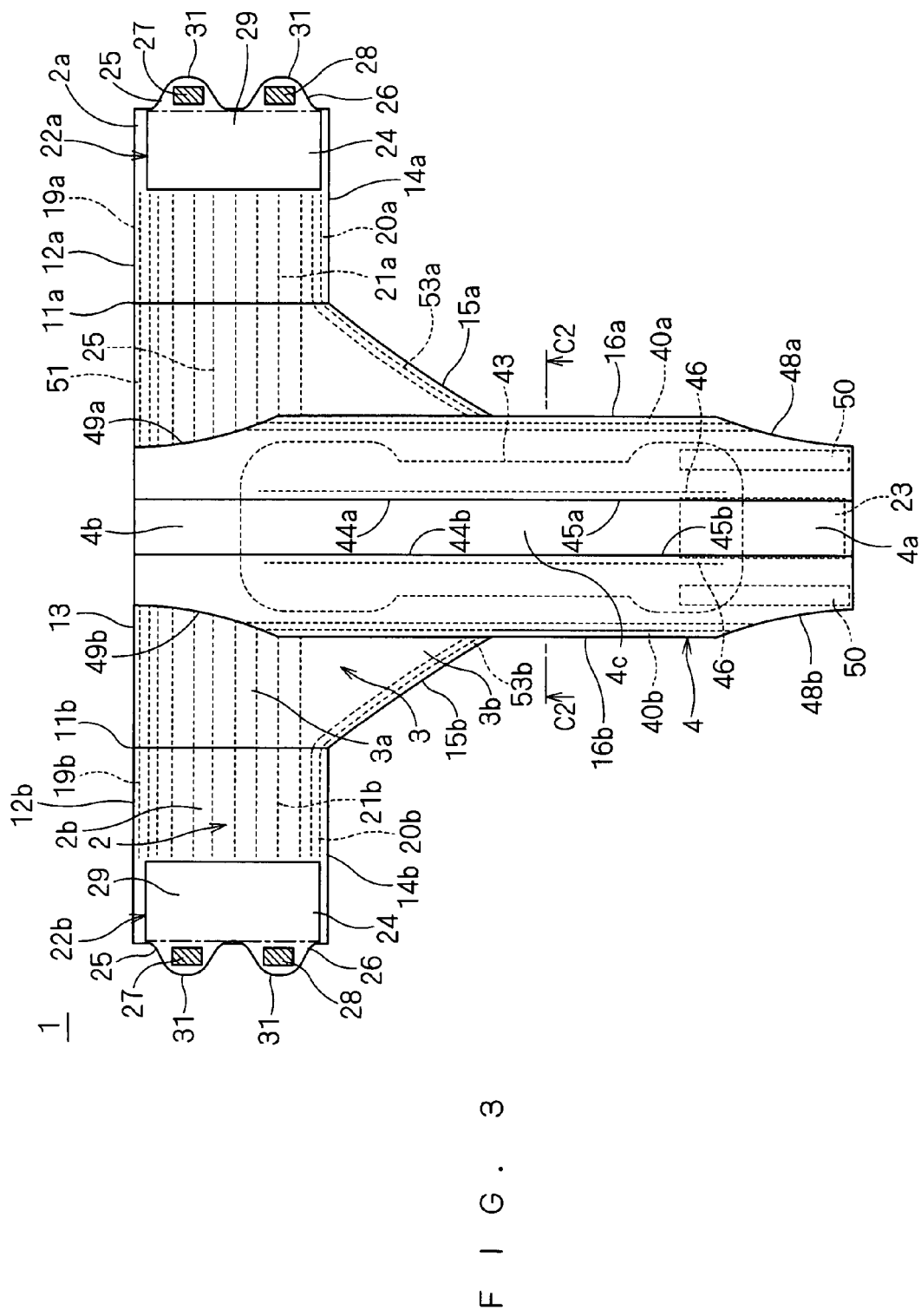
FIG. 3 is a diagram showing the state in which a crotch section of the disposable pants shown in FIG. 1 is developed.

Further, the pants 1 may be used as a typical disposable diaper by applying the pants 1 in the configuration shown in FIG. 3 around the wearer's hips and then closing them in the order of FIGS. 3, 2 and 1. In this case, the pants 1 can be put on and removed without taking off the wearer's garments.

Further, when using the pants 1 with the breaking line parts 17a and 17b broken, the adhesive pieces 22a and 22b may be secured so as to overlap each other in the case where the wearer has slim hips. That is, with a first adhesive piece 22a (or 22b) being secured to the adhesive part 23, the second adhesive piece 22b (22a) may be secured to the adhesive part 23 and the like so as to overlap the first adhesive piece 22a (or 22b).

<Crotch Section>

The crotch section 4 has an almost strip shape extending in the front-to-rear direction (cf. FIGS. 3 and 4), and includes the front crotch part 4a, rear crotch part 4b, and central crotch part 4c which is positioned midway between them, and is applied to the wearer such that the crotch of a wearer is mainly in the central crotch part 4c at the center. The front crotch part 4a is bonded to the central front abdominal part 2c by the bonding part 18 while overlapping the interior side of the central front abdominal part 2c (cf. FIG. 1). The rear crotch part 4b is bonded and fixed to the rear section 3 while overlapping the interior side of the rear section 3 (cf. FIGS. 3 and 4). Leg elastic members 40a and 40b are attached to the left edge 16a and right edge 16b of such crotch section 4 in a stretched state in the direction that the edges 16a and 16b extend.

Figure 6:
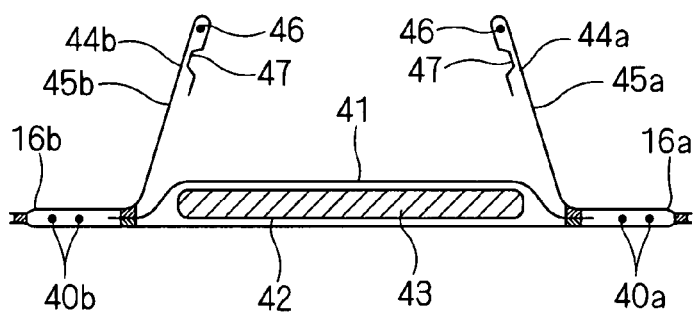
FIG. 6 is a sectional view taken along line C1-C1 of the disposable pants shown in FIG. 1.

The crotch section 4 is formed by sandwiching the absorber 43 between a liquid-permeable top sheet 41 and a liquid-impermeable backsheet 42 (cf. FIGS. 3 and 6). The absorber 43 has a predetermined width and extends in the front-to-rear direction in the form of strip with the central crotch part 4c at the center. The left and right sides of the absorber 43 on the interior side of the crotch section 4 are provided with standing parts 44a and 44b extending in the direction that the crotch section 4 extends.

For instance, the top sheet 41 is made of a liquid-permeable nonwoven fabric or the like, and the backsheet 42 is made of a water-repellant nonwoven fabric or the like. The absorber 43 is formed, for example, by covering a mass of a hydrophilic fiber assembly layer such as crushed pulp fibers or cellulose fibers mixed with a particulate gelling agent, with a covering sheet such as a sheet of paper like tissue paper, a liquid-permeable nonwoven sheet or the like, and is formed in a predetermined shape.

As to areas of the top sheet 41 and backsheet 42 that do not overlap the absorber 43, surfaces facing each other are bonded to each other with an adhesive such as a hot melt adhesive. More preferably, the width of the top sheet 41 is set to cover the skin-facing side of the absorber 43 and to be slightly narrower than the width of the backsheet 42, and portions of the top sheet 41 extending off the absorber 43 in the front-to-rear and lateral directions are bonded to the backsheet 42 with an adhesive such as a hot melt adhesive. Left and right side sheets 45a and 45b constituting the standing parts 44a and 44b are bonded to the skin-facing side of portions of the backsheet 42 extending off the top sheet 41 in the both lateral directions with an adhesive such as a hot melt adhesive.

Further, the edges of the side sheets 45a and 45b in the front-to-rear direction are bonded to the edges of the crotch section 4 in the front-to-rear direction with an adhesive 60 such as a hot melt adhesive (cf. FIG. 5). The laterally inside edges of the side sheets 45a and 45b are fixed by heating welding (or ultrasonic welding) or the like with sealing parts 47 so as to enclose elastic members 46 extending in the front-to-rear direction. The standing parts 44a and 44b have their laterally inside edges contracted by the contractive force of the elastic members 46, and are thereby raised in a direction so as to press against the wearer's skin.

Furthermore, in the present embodiment, left and right edges of the area of the crotch section 4 that overlaps the front abdominal section 2 and a waist zone 3a of the rear section 3 are sloped edges 48a, 48b, 49a and 49b, and has a gradually tapered width which gradually tapers toward the edges in the front-to-rear direction (cf. FIG. 3).

These sloped edges 48a and 48b prevent the front crotch part 4a from curling up, becoming bent, or affecting the wearer's skin when raising/lowering the disposable pants 1, which allows smooth raising/lowering.

Further, the contractive force of the rear section 3 generally tends to decrease in an area where the rear section 3 and crotch section 4 overlap, however, forming a trim area by the aforementioned sloped edges 49a and 49b gradually increases the area of the elastic part of the rear section 3 toward the top side of the rear section 3, which allows the rear section 3 to easily fit the wearer's back.

Figure 4:
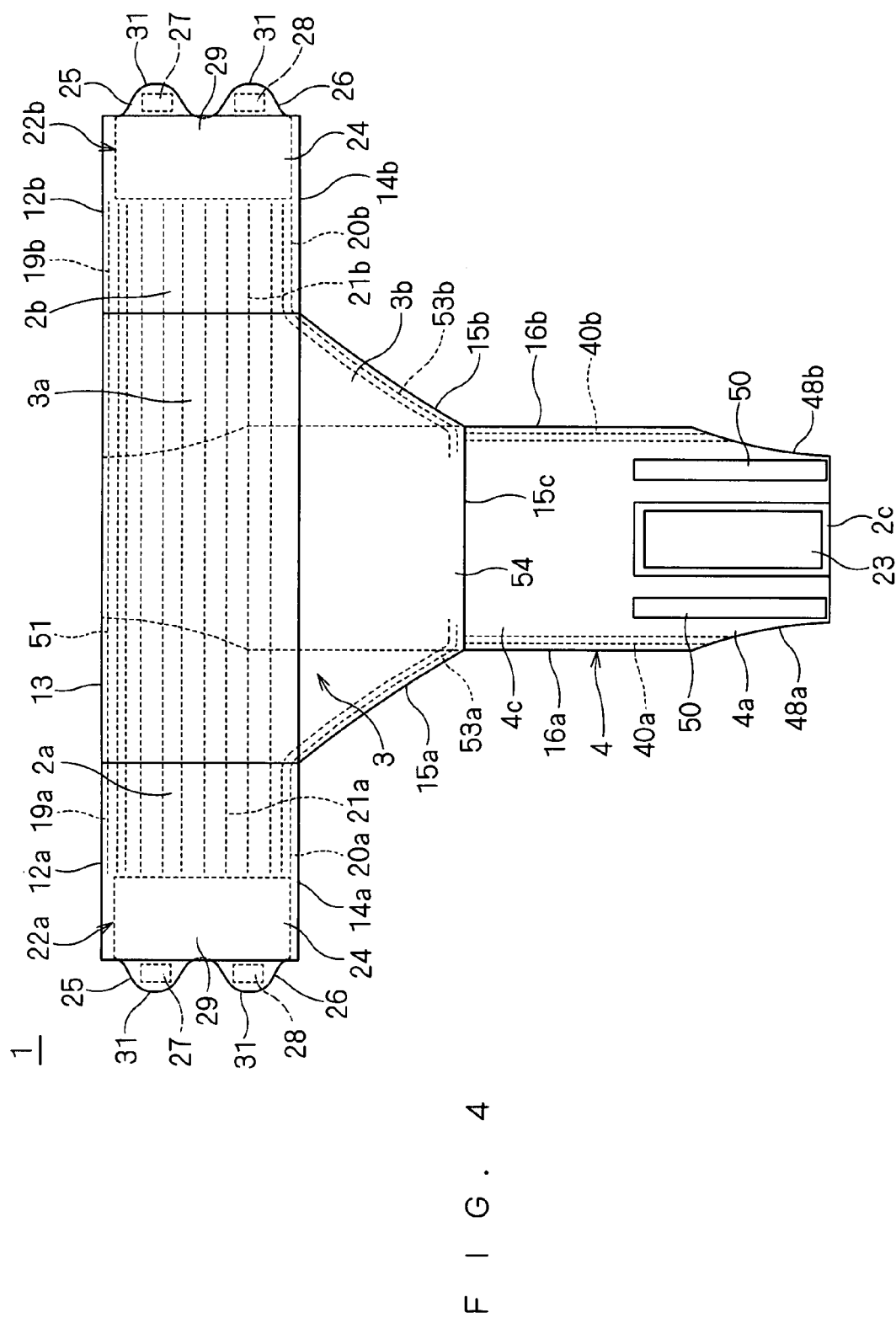
FIG. 4 is a diagram of the disposable pants shown in FIG. 3 as viewed from the opposite side to FIG. 3.

Further, the adhesive part 50 is provided on the edges of the crotch section 4 on the side of the front abdominal section 2 (cf. FIGS. 2 and 4). This adhesive part 50 is formed in the position facing the adhesive part 29 on the interior side of the adhesive pieces 22a and 22b. The adhesive part 50 is configured to be detachably secured to the adhesive part 29 on the interior side of the adhesive pieces 22a and 22b, with the adhesive parts 27 and 28 of the adhesive pieces 22a and 22b being secured to the aforementioned adhesive part 23 (cf. FIG. 8).

As a variation of structure of the crotch section 4, the absorber 43 may be adhered to the skin-facing side of the sheet 42, rather than sandwiched between the sheets 41 and 42, and the sheet 41 may be omitted. Alternatively, the absorber 43 with sheets bonded to its front and rear edges may be used as the crotch section 4, or a large absorber 43 may be used as the crotch second 4, and the sheets 41 and 42 may be omitted.

<Rear Section>

The rear section 3 has such a form that, when developed, left and right lower side corners of almost rectangle are cut almost diagonally, and is applied to an area from the waist to hips on the wearer's back (cf. FIGS. 3 and 4). For this purpose, this rear section 3 includes the waist zone 3a in the form of almost laterally long strip in plan view mainly positioned on the waist on the wearer's back and a hip zone 3b of almost trapezoidal form in plan view joined downwardly to the waist zone 3a and mainly positioned on the wearer's hips. A waist elastic member 51 is attached in a laterally stretched state to the upper edge 13 of the waist zone 3a. A body elastic member 52 is attached in a laterally stretched state to the other area of the waist zone 3a. A leg elastic member 53a is attached to the sloped edge 15a on the left lower side of the rear section 3 in a stretched state along the edge 15a. A leg elastic member 53b is attached to the sloped edge 15b on the right lower side of the rear section 3 in a stretched state along the edge 15b. Contraction and stretch of these elastic members 51, 52, 53a and 53b allows the rear section 3 to easily fit the wearer's back and hips.

Particularly, the hip zone 3b of the rear section 3 has a width that gradually tapers downwardly, and its left and right sloped edges 15a and 15b provided with the leg elastic members 53a and 53b. Therefore, the hip zone 3b easily fits the wearer's hips when the edges 15a and 15b are contracted by the contractive forces of the leg elastic members 53a and 53b.

The leg elastic members 53a and 53b are continuously attached to the hip zone 3b along the left and right sloped edges 15a and 15b and lower edge 15c of the hip zone 3b, and then, at least an area 54 (cf. FIG. 4) overlapping the absorber 43 of the crotch section 4 is subjected to a weakening process. The weakening process is a process of cutting the elastic member in that area 54 or weakening its contractive force, or the like, to thereby bring about a no-tension state. This prevents the absorber 43 from suffering from an undesired contortion due to the contractive forces of the leg elastic members 53a and 53b and from degrading in its absorptive function.

<Other Structure and Material for Respective Parts, etc.>

As to the left and right elastic members 19a, 19b, elastic members 20a, 20b, and elastic members 21a, 21b provided in the front abdominal section 2, similar to the case of the aforementioned leg elastic members 53a and 53b, it is preferable that the elastic members 20a, 20b, 21a and 21b be provided laterally continuously in the front abdominal section 2 through the central front abdominal part 2c, and then portions of the elastic members 20a, 20b, 21a and 21b positioned in the central front abdominal part 2c be subjected to the weakening process.

Further, the material for the adhesive pieces 22a and 22b may be selected from appropriate nonwoven fabrics, woven fabrics, knitted fabrics and plastic materials. Among them, a nonwoven fabric manufactured by one or a combination of a plurality of processes among spun-bond process, air-through process, point-bond process, melt-blow process and air-laid process is preferable. Further, a nonwoven fabric manufactured by a spun-bond process or a SMS process combining the spun-bond process and a melt-blow process with a weight of 30 to 100 g/m$^2$ is preferable in terms of strength. Most preferable is a nonwoven fabric manufactured by the spun-bond process with a weight of 50 to 85 g/m$^2$. The material can be selected from appropriate synthetic fibers such as polypropylene, polyethylene, polyester, polyamide and the like and natural fibers such as pulp, silk and the like, but preferably, a synthetic fiber such as polypropylene, polyethylene or polyester can be used, and among them, one having a polypropylene or polyester fiber as its main component is strong and suitable. The most preferable one is a polyester fiber.

Further, for the elastic members 19a, 19b, 20a, 20b, 21a, 21b, 40a, 40b, 46, 53a and 53b, an elastic stretchable material (polyurethane thread, polyurethane film, natural rubber, etc.) typically used for disposable pants is employed, and is attached to a specified position of the pants 1 in a stretched state by an adhering means such as a hot melt adhesive, heating welding, ultrasonic welding or the like.

In the disposable pants, the adhesive pieces 22a and 22b are provided on the interior side of the front abdominal section 2. This prevents the adhesive pieces 22a and 22b from becoming obstacles, allowing easy recognition of the breaking line parts 17a and 17b from the outside. Further, when breaking at the breaking line parts 17a and 17b, the adhesive pieces 22a and 22b are unlikely to obstruct the breaking operation. This allows the breaking operation to be performed easily.

Further, the projections 25 and 26 of the adhesive pieces 22a and 22b that extend beyond the breaking line parts 17a and 17b are configured to be folded back toward their base sides. Accordingly, the breaking line parts 17a and 17b extend without crossing over the adhesive pieces 22a and 22b. Hence, when breaking at the breaking line parts 17a and 17b, the adhesive pieces 22a and 22b are unlikely to obstruct the breaking operation with more reliability, which allows the breaking operation to be performed easily.

Besides, the adhesive parts 27 and 28 provided on one side surface of the adhesive pieces 22a and 22b are provided in areas laterally inward from the outer edges of the adhesive pieces 22a and 22b, which thus can effectively prevent contact of the outer edges of the adhesive parts and the wearer's skin, etc.

That is, since the adhesive pieces 22a and 22b are provided on the interior side of the front abdominal section 2, the adhesive pieces 22a and 22b may be in direct contact with the wearer's skin in the case where the both side edges of the front crotch part 4a are curled up, or in the case where the width of the front crotch section 4a is narrow. Here, since the projections 25 and 26 of the adhesive pieces 22a and 22b are folded to be folded back, the main surfaces of the adhesive parts 27 and 28 are, basically, not in direct contact with the wearer's skin.

However, since the adhesive parts 27 and 28 are formed to reach the outer edges of the projections 25 and 26, the outer edges of the adhesive parts 27 and 28 may touch the wearer's skin on the outer edges of the projections 25 and 26 to cause unpleasantness such as itching. Accordingly, as described above, by providing the adhesive parts 27 and 28 in areas laterally inward from the outer edges of the adhesive pieces 22a and 22b, contact between the outer edges of the adhesive parts 27 and 28 and the wearer's skin, etc. can effectively be prevented, which hence can contribute to pleasantness in wearing.

Second Embodiment

With reference to FIGS. 9 to 14, disposable pants according to a second embodiment of the present invention will be described. This second embodiment has adhesive pieces 122a and 122b which are folded to expose the breaking line parts 17a and 17b to the outside. In the following description of the second embodiment, components similar to those described in the first embodiment are indicated by the same reference numerals, and their explanations are omitted.

In disposable pants 101 according to this second embodiment, instead of the configuration in which the adhesive pieces 22a and 22b are provided on the interior side of the front abdominal section 2 as in the first embodiment, the adhesive pieces 122a and 122b are provided on the exterior side of the front abdominal section 2 and are folded midway.

More specifically, the adhesive pieces 122a and 122b have a structure similar to the aforementioned adhesive pieces 22a and 22b, and each includes an almost vertically long strip body 124 and two projections 125 and 126 bifurcated, one on top of the other, extending from the body 124 toward its free edge side.

Figure 13:
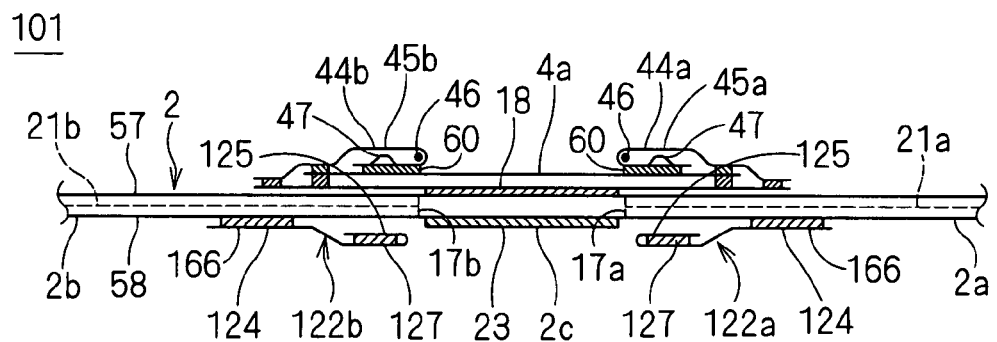
FIG. 13 is a sectional view taken along line C3-C3 of the disposable pants shown in FIG. 1.
Figure 14:
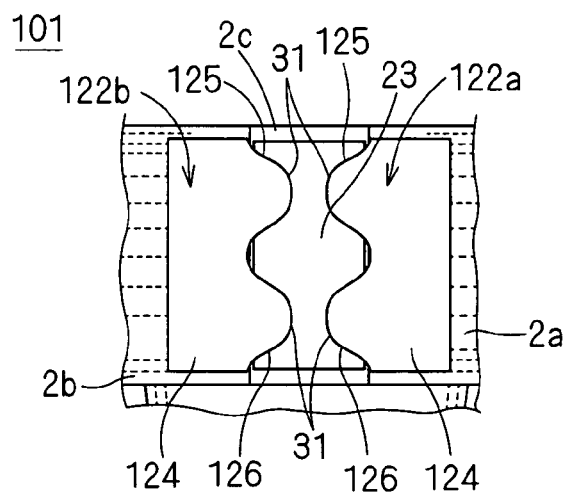
FIG. 14 is a diagram showing the state in which left and right adhesive pieces are secured to a central front abdominal part.

The laterally outside edges of the body 124 are bonded to the exterior side of the left front abdominal part 2a and right front abdominal part 2b, close to the edges thereof, and on the side of the breaking line parts 17a and 17b by an adhesive 166, e.g., hot melt adhesive (cf. FIG. 13).

Besides, portions of the adhesive pieces 122a and 122b that extend beyond the breaking line parts 17a and 17b (here, projections 125 and 126) are folded to be folded back toward their base sides along lines short of the breaking line parts 17a and 17b (cf. FIGS. 1 and 5). Accordingly, the breaking line parts 17a and 17b are not hidden by the adhesive pieces 122a and 122b, and can be recognized from the front of the front abdominal section 2.

Particularly, the adhesive pieces 122a and 122b are folded in such a manner that the projections 125 and 126 which are the tips of the adhesive pieces 122a and 122b are folded back toward the inside. More specifically, the projections 125 and 126 are folded back into positions interposed between the base sides of the adhesive pieces 122a, 122b and front abdominal section 2.

In this state, the projections 125 and 126, which are folded portions of the adhesive pieces 122a and 122b, may be temporarily secured to the front abdominal section 2. As temporary securing means, heating welding, ultrasonic welding, adhesive (e.g., hot melt adhesive), etc. may be considered, and the adhesive pieces 122a, 122b and front abdominal section 2 are bonded with a strength that enables them to be peeled apart.

Further, adhesive parts 127 and 128 are provided on the interior side of the respective projections 125 and 126 of the adhesive pieces 122a and 122b, respectively (on the surface facing the adhesive part 23 when the pants 1 are used in the form of diaper). Here, since the respective projections 125 and 126 are folded back in the aforementioned form, the adhesive parts 127 and 128 are directed to the exterior side of the front abdominal section 2 and are in contact with the interior side of the body 124 (cf. FIG. 13). The adhesive parts 127 and 128 are present on the peripheral side of the front abdominal section 2, and are not in contact with the wearer's skin. Therefore, unlike the adhesive parts 27 and 28 in the first embodiment, the adhesive parts 127 and 128 are not required to be provided in areas laterally inward from the outer edges of the adhesive pieces 122a and 122b.

In the disposable pants 101, the adhesive parts 29 and 50 are omitted.

When the disposable pants 101 are used in the form of pants, the breaking line parts 17a and 17b are not broken, and the projections 125 and 126 of the adhesive parts 122a and 122b are kept folded back, that is, kept in the a shipping form.

On the other hand, when the disposable pants 101 are used as a diaper, first, the breaking line part 17a is broken. At this time, since the breaking line parts 17a and 17b are exposed to the outside without being hidden by the adhesive pieces 122a and 122b, the breaking operation can be carried out while visually recognizing the breaking line parts 17a and 17b. Then, the projections 125 and 126 on the tips of the adhesive pieces 122a and 122b are pulled to extend out from the ends of the interior side of the left and right front abdominal parts 2a and 2b (cf. FIGS. 11 and 12). In the worn state, the adhesive parts 27 and 28 on the projections 25 and 26 of the adhesive pieces 22a and 22b are secured to the aforementioned adhesive part 23 (cf. FIG. 14).

In the disposable pants 101, since the adhesive pieces 122a and 122b are folded such that the breaking line parts 17a and 17b are exposed to the outside, the breaking line parts 17a and 17b can be easily recognized from the outside. Further, the adhesive pieces 122a and 122b are unlikely to obstruct breaking at the breaking line parts 17a and 17b, which allows the breaking operation to be carried out easily. In addition, there is an advantage that the adhesive pieces 122a and 122b are easily recognized from the outside, which allows a connecting operation using the adhesive pieces 122a and 122b, and the like to be carried out easily.

Further, since the adhesive pieces 122a and 122b are folded such that the projections 125 and 126 on the tips of the adhesive pieces 122a and 122b are folded toward the inside, the tips of the adhesive pieces 122a and 122b are unlikely to be loose during shipping, or when the diaper 101 is used in the form of pants, and the like.

Variation

While the aforementioned embodiments have described the example in which the adhesive pieces 22a, 22b, 122a, 122b are provided on the left and right front abdominal parts 2a and 2b, they may be provided on the central front abdominal part 2c.

Further, the aforementioned breaking line parts 17a and 17b may be colored differently from the base color. For instance, in the case where the front abdominal section 2 is formed of a white material, the breaking line parts 17a and 17b may be colored light blue.

In this case, the breaking line parts 17a and 17b can be recognized relatively easily, and therefore, the breaking operation at the breaking line parts 17a and 17b can be carried out more easily.

While the invention has been shown and described in detail, the foregoing description is in all aspects illustrative, and the invention is not limited thereto. It is therefore understood that numerous modifications and variations can be devised without departing from the scope of the invention.

The invention claimed is:
1. Disposable pants comprising:
a front abdominal section having a central part, a left part, and a right part, wherein a first breaking line is formed in said front abdominal section between the right part and the central part, and a second breaking line is formed in said front abdominal section between the left part and the central part;
a rear section connected to opposite ends of said front abdominal section such that an interior side of said front abdominal section opposes an interior side of said rear section;
a crotch section connected to said rear section and to the central part of said front abdominal section;
an absorber provided on said crotch section;
a first adhesive piece disposed on said front abdominal section for re-connecting the right part of said front abdominal section to the central part of said front abdominal section after breaking the first breaking line; and
a second adhesive piece disposed on said front abdominal section for re-connecting the left part of said front abdominal section to the central part of said front abdominal section after breaking the second breaking line,
wherein said first and second adhesive pieces are located on said front abdominal section so that the first and second breaking lines are exposed at an exterior side of said front abdominal section, wherein said adhesive pieces are disposed on the interior side of said front abdominal section, and wherein the front abdominal section has a laterally-long rectangular shape, and left and right edges of the front abdominal section are bonded to left and right edges of the rear section such that the front abdominal section and the rear section are joined almost annularly.

2. The disposable pants of claim 1, wherein said adhesive pieces are disposed on the central part of said front abdominal section.

3. The disposable pants of claim 1, wherein said adhesive pieces are disposed on the right and left parts of said front abdominal section.

4. The disposable pants of claim 2, wherein each of said adhesive pieces includes at least one adhesive part for detachably attaching to the right and left parts of said front abdominal section, said adhesive parts being disposed within a peripheral edge of said adhesive pieces.

5. The disposable pants of claim 3, wherein each of said adhesive pieces includes at least one adhesive part for detachably attaching to the central part of said front abdominal section, said adhesive parts being disposed within a peripheral edge of said adhesive pieces.

6. The disposable pants of claim 3, wherein each of said adhesive pieces includes a body portion and a projection which is folded back such that a surface thereof opposes a surface of said body portion prior to breaking the first and second breaking lines.

7. The disposable pants of claim 6, wherein said rear section and the right and left parts of said front abdominal section are stretchable in a lateral direction.

8. The disposable pants of claim 6, wherein said adhesive parts are hooked members, and the central part of said front abdominal section comprises a looped member for detachably engaging with said hooked members.

9. The disposable pants of claim 6, further comprising an additional adhesive part disposed on said crotch section beside the central part of said front abdominal section for detachably engaging with an interior facing surface of at least one of said body portions.

10. Disposable pants comprising:
a front abdominal section having a central part, a left part, and a right part;
a first breaking line formed in said front abdominal section between the right part and the central part;
a second breaking line formed in said front abdominal section between the left part and the central part;
a rear section connected to opposite ends of said front abdominal section such that an interior side of said front abdominal section opposes an interior side of said rear section;
a crotch section connected to said rear section and to the central part of said front abdominal section;
an absorber provided on said crotch section;
a first adhesive piece disposed on said front abdominal section for re-connecting the right part of said front abdominal section to the central part of said front abdominal section after breaking the first breaking line; and
a second adhesive piece disposed on said front abdominal section for re-connecting the left part of said front abdominal section to the central part of said front abdominal section after breaking the second breaking line, wherein said first and second adhesive pieces are located on said front abdominal section so that the first and second breaking lines are exposed at an exterior side of said front abdominal section, wherein said first breaking line is disposed on a front of said disposable pants between said central part of said front abdominal section and said first adhesive piece, and said first adhesive piece is disposed beneath an exterior surface of the front abdominal section, wherein said second breaking line is disposed on a front of said disposable pants between said central part of said front abdominal section and said second adhesive piece, and said second adhesive piece is disposed beneath an exterior surface of the front abdominal section, and wherein the front abdominal section has a laterally-long rectangular shape, and left and right edges of the front abdominal section are bonded to left and right edges of the rear section such that the front abdominal section and the rear section are joined almost annularly.

11. The disposable pants of claim 10, wherein said first adhesive piece is folded back away from said first breaking line, and said second piece is folded back away from said second breaking line, wherein said first adhesive piece unfolds to extend beyond said right part of said front abdominal section so as to connect to said central part of said front abdominal section, and wherein said second adhesive piece unfolds to extend beyond said left part of said front abdominal section so as to connect to said central part of said front abdominal section.

12. The disposable pants of claim 10, wherein the first adhesive piece and the second adhesive piece each include a body portion disposed beneath the exterior surface of the front abdominal section and a projection which extends from the front abdominal section, and wherein an adhesive part is provided on each of the projections.

13. The disposable pants of claim 12, wherein the adhesive parts do not extend onto tips of the projections, such that the tip of each projection forms a tab which does not have an adhesive part.

14. The disposable pants of claim 10, wherein each of said adhesive pieces includes a body portion and a projection, the body portion being disposed beneath the exterior surface of the front abdominal section and being connected to the front abdominal section, and the projection extending from the body portion for re-connecting to the central part of the front abdominal section, wherein each of the projections is folded back such that a surface of the projection opposes a surface of the body portion prior to breaking the first and second breaking lines, wherein an adhesive part is provided on each of the projections for detachably attaching to the right and left parts of said front abdominal section, and wherein the adhesive parts are disposed on the opposing surfaces of the tabs which face the body portions when the tabs are folded back.

15. The disposable pants of claim 14, wherein the adhesive parts do not extend onto tips of the projections, such that the tip of each projection forms a tab which does not have an adhesive part.

16. The disposable pants of claim 1, wherein the first adhesive piece and the second adhesive piece include projections which extend from the front abdominal section, and wherein an adhesive part is provided on each of the projections.

17. The disposable pants of claim 16, wherein the adhesive parts do not extend onto tips of the projections, such that the tip of each projection forms a tab which does not have an adhesive part.

18. The disposable pants of claim 1, wherein each of said adhesive pieces includes a body portion and a projection, the body portion being connected to the interior side of the front abdominal section and the projection extending from the body portion for re-connecting to the central part of the front abdominal section, wherein each of the projections is folded back such that a surface of the projection opposes a surface of the body portion prior to breaking the first and second breaking lines, wherein an adhesive part is provided on each of the projections for detachably attaching to the right and left parts of said front abdominal section, and wherein the adhesive parts are disposed on the opposing surfaces of the tabs which face the body portions when the tabs are folded back.

19. The disposable pants of claim 18, wherein the adhesive parts do not extend onto tips of the projections, such that the tip of each projection forms a tab which does not have an adhesive part.

* * * * *